(12) United States Patent
Winnicki et al.

(10) Patent No.: US 9,359,625 B2
(45) Date of Patent: Jun. 7, 2016

(54) CHEMICAL ENGINEERING PROCESSES AND APPARATUS FOR THE SYNTHESIS OF COMPOUNDS

(71) Applicant: FULL SPECTRUM LABORATORIES LIMITED, Dublin (IE)

(72) Inventors: Robert Winnicki, Vancouver (CA); Marc Donsky, Vancouver (CA)

(73) Assignee: Full Spectrum Laboratories Limited, Dublin (IE)

( * ) Notice: Subject to any disclaimer, the term of this patent is extended or adjusted under 35 U.S.C. 154(b) by 0 days.

(21) Appl. No.: 14/836,339

(22) Filed: Aug. 26, 2015

(65) Prior Publication Data

US 2015/0361469 A1 Dec. 17, 2015

Related U.S. Application Data

(63) Continuation of application No. PCT/US2014/018944, filed on Feb. 27, 2014.

(60) Provisional application No. 61/770,766, filed on Feb. 28, 2013.

(51) Int. Cl.
| | |
|---|---|
| *A61K 31/352* | (2006.01) |
| *C12N 9/04* | (2006.01) |
| *C12N 11/02* | (2006.01) |
| *C12P 17/06* | (2006.01) |
| *C12M 1/40* | (2006.01) |
| *C12M 1/34* | (2006.01) |
| *A61K 38/00* | (2006.01) |

(52) U.S. Cl.
CPC .............. *C12P 17/06* (2013.01); *A61K 31/352* (2013.01); *C12M 21/18* (2013.01); *C12M 41/30* (2013.01); *C12Y 121/03007* (2015.07); *C12Y 121/03008* (2015.07)

(58) Field of Classification Search
None
See application file for complete search history.

(56) References Cited

U.S. PATENT DOCUMENTS

| | | | |
|---|---|---|---|
| 2004/0053386 A1 | 3/2004 | Chappell et al. | |
| 2006/0183211 A1 | 8/2006 | Kuzuyama et al. | |
| 2010/0298579 A1* | 11/2010 | Steup | C07C 37/50 549/390 |
| 2012/0322114 A1* | 12/2012 | Liu | C12P 19/64 435/101 |
| 2013/0067619 A1* | 3/2013 | Page | C12N 9/1025 800/278 |
| 2015/0361469 A1 | 12/2015 | Winnicki et al. | |
| 2016/0053220 A1 | 2/2016 | Peet et al. | |

FOREIGN PATENT DOCUMENTS

| | | |
|---|---|---|
| WO | WO-2011/127589 A1 | 10/2011 |
| WO | WO 2011/127589 A1 | 10/2011 |
| WO | WO-2014/134281 A1 | 9/2014 |

OTHER PUBLICATIONS

Flemming et al. (2007) Chemistry and Biological Activity of Tetrahydrocannabinol and its Derivatives, TopHeterocyl. Chem., vol. 110, pp. 1-42.*
Morimoto, Satoshi, et al.; "Enzymological Evidence for Cannabichromenic Acid Biosynthesis"; *Journal of Natural Products*; Aug. 1997; vol. 60, No. 8; pp. 854-857.
Taura, Futoshi; "Studies on tetrahydrocannabinolic acid synthase that produces the acidic precursor of tetrahydrocannabinol, the pharmacologically active cannabinoid in marijuana"; *Drug Discoveries & Therapeutics*, Jun. 2009; vol. 3, No. 3; pp. 83-87.
Sanchez, Isvett Josefina Flores; "Polyketide synthases in *Cannabis sativa* L"; *Phytochem Rev* (2008); pp. 1-169.
Thakur, Ganesh A., et al.; "Natural cannabinoids: Templates for drug discovery"; *Life Sciences* 78 (2005); pp. 454-466.
PCT International Search report on application PCT/US14/18944 mailed Jun. 9, 2014; 2 pages.

(Continued)

*Primary Examiner* — Anand Desai
*Assistant Examiner* — Samuel Liu
(74) *Attorney, Agent, or Firm* — Foley & Lardner LLP

(57) ABSTRACT

The present invention provides methods for producing cannabinoids and cannabinoid analogs as well as a system for producing these compounds. The inventive method is directed to contacting a compound according to Formula I or Formula II with a cannabinoid synthase.

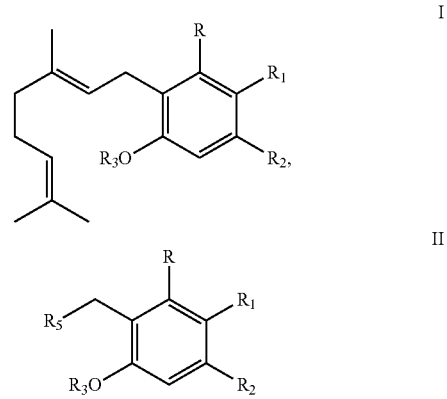

Also described is a system for producing cannabinoids and cannabinoid analogs by contacting a THCA synthase with a cannabinoid precursor and modifying at least one property of the reaction mixture to influence the quantity formed of a first cannabinoid relative to the quantity formed of a second cannabinoid.

19 Claims, 1 Drawing Sheet

(56) References Cited

OTHER PUBLICATIONS

F. Taura et al., "Purification and Characterization of Cannabidiolic-acid Synthase from *Cannabis sativa* L.: Biochemical Analysis of a Novel Enzyme That Catalyzes the Oxidocyclization of Cannabigerolic Acid to Cannabidiolic Acid", Journal of Biological Chemistry, Jul. 19, 1996, pp. 17411-17416, vol. 271, No. 29.

Futoshi Taura et al., "First Direct Evidence for the Mechanism of Δ1-Tetra hydrocannabinolic Acid Biosynthesis", J. Am. Chem. Soc. J. Am. CheM, Jan. 1, 1995, pp. 9766-9767, Retrieved from the Internet: URL:http://pubs.acs.org/doi/pdf/10.1021/ja00143a024.

Kerstin Lange et al., "Enrichment and identification of Δ9-Tetrahydrocannabinolic acid synthase from Pichia pastoris supernatants", Data in Brief, Sep. 2015, pp. 641-649, vol. 4.

Kerstin Lange et al., "Δ9-Tetrahydrocannabinolic acid synthase production in Pichia pastoris enables chemical synthesis of cannabinoids", Journal of Biotechnology, Oct. 1, 2015, pp. 68-76, vol. 211, NL.

PCT International Search Report and Written Opinion on application PCT/IB2015/056445 mailed Dec. 10, 2015; 18 pages.

Sanja Martens et al., "Fully automated production of potential Malaria vaccines with Pichia pastoris in integrated processing", Engineering in Life Sciences, Aug. 1, 2011, pp. 429-435, vol. 11, No. 4, DE.

Taura et al., "Cannabidiolic-acid synthase, the chemotype-determining enzyme in the fiber-type Cannabis sativa", Febs Letters, Jun. 14, 2007, pp. 2929-2934, vol. 581, No. 16, Elsevier B.V., Amsterdam, NL.

Taura et al., "Production of Δ1-tetrahydrocannabinolic acid by the biosynthetic enzyme secreted from transgenic Pichia pastoris"; Biochemical and Biophysical Research Communications vol. 361 No. 3 (2007); Sep. 28, 2007; pp. 675-680; Elsevier Inc.

USPTO Non-final Office Action issued in U.S. Appl. No. 14/835,444 dated Feb. 25, 2016; 8 pages.

Zirpel Bastian et al., "Production of Δ9-terahydrocannabinolic acid from cannabigerolic acid by whole cells of Pichia (Komagataella) pastoris expressing Δ9-tetrahydrocannabinolic acid synthase from Cannabis sativa", Biotechnology Letters, May 21, 2015, pp. 1869-1875, vol. 37, No. 9, Springer Netherlands, NL.

\* cited by examiner

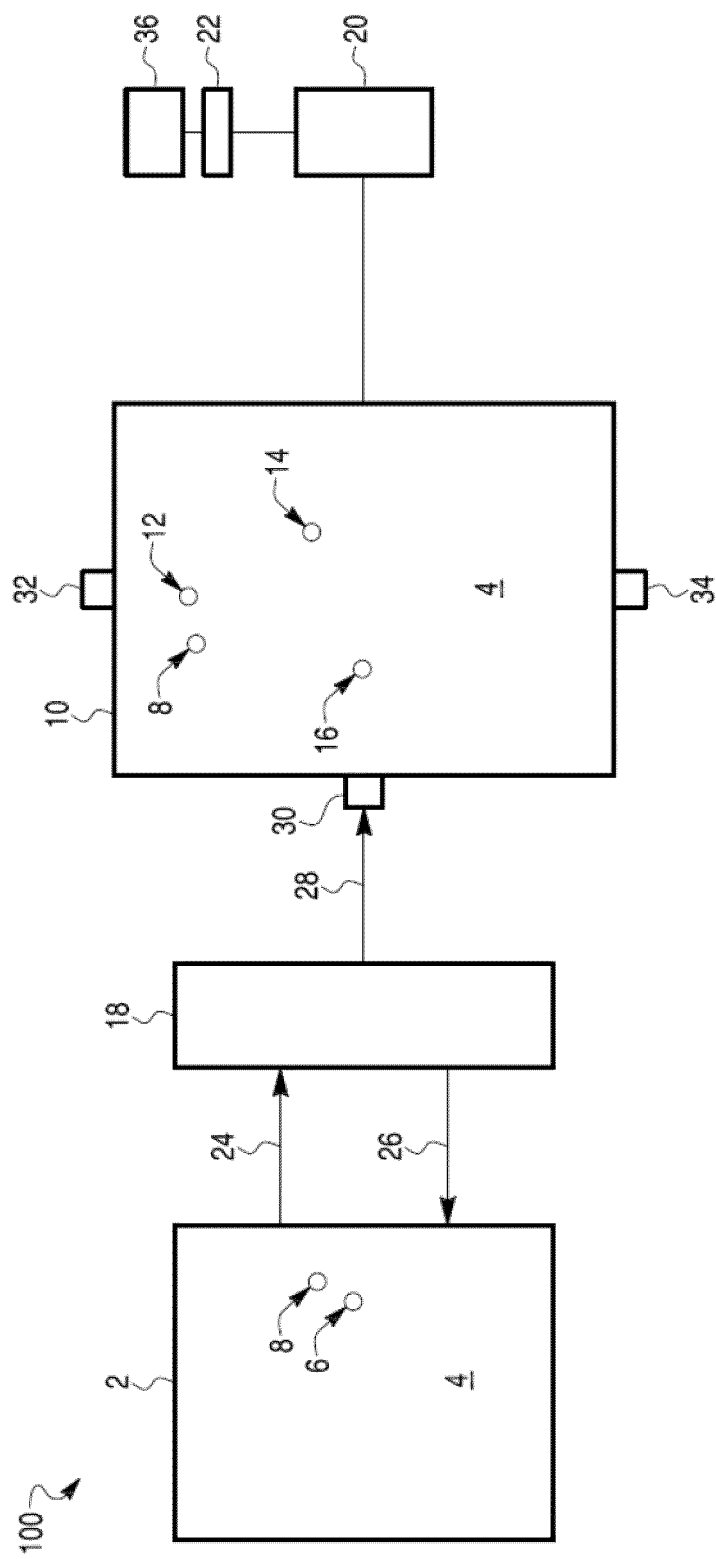

CHEMICAL ENGINEERING PROCESSES AND APPARATUS FOR THE SYNTHESIS OF COMPOUNDS

CROSS-REFERENCE TO RELATED PATENT APPLICATIONS

This application is a Continuation of PCT Application PCT/US2014/018944, filed Feb. 27, 2014, incorporated herein by reference in its entirety, which claims priority from U.S. Provisional Application 61/770,766, filed Feb. 28, 2013, incorporated herein by reference in its entirety.

FIELD OF THE INVENTION

This application claims the benefit of priority from U.S. Provisional Patent Application No. 61/770,766, filed on Feb. 28, 2013, the content of which are incorporated by reference.

The present invention relates to biosynthesis of cannabinoids. More specifically, this invention relates to methods for using protein kinase synthase enzymes, responsible for the synthesis of cannabinoids in plants, to manufacture ex vivo milligram to gram or kilogram quantities of cannabinoids suitable for pharmaceutical and nutraceutical applications.

BACKGROUND OF THE INVENTION

Cannabinoids are compounds derived from *Cannabis sativa*, an annual plant in the Cannabaceae family. The plant contains about 60 cannabinoids. The most well-known naturally occurring cannabinoid is tetrahydrocannabinol (THC), which is used for the treatment of a wide range of medical conditions, including glaucoma, AIDS wasting, neuropathic pain, treatment of spasticity associated with multiple sclerosis, fibromyalgia and chemotherapy-induced nausea. Additionally, THC has been reported to exhibit a therapeutic effect in the treatment of allergies, inflammation, infection, epilepsy, depression, migraine, bipolar disorders, anxiety disorder, and drug dependency and withdrawal syndromes. THC is particularly effective as an anti-emetic drug and is administered to curb emesis, a common side effect accompanying the use of opioid analgesics and anesthetics, highly active anti-retroviral therapy and cancer chemotherapy.

Cannabinoids are increasingly being used for pharmaceutical and nutraceutical applications. Cannabinoid compounds used in such applications are almost exclusively obtained from natural sources, for example, from plant tissue. Thus, the prior art discloses obtaining cannabinoid compounds from the trichomes of the *C. sativa* plant using different solvent extraction methodologies. Some draw backs associated with such methods include poor yields, high costs associated with growing and maintenance of the plant and costs associated with extraction and purification of the plant extract. Security of plants is also an important consideration that adds to the cost of producing pharmaceutical grade cannabinoid compounds.

However, the increasing importance of cannabinoid compounds, particularly, for treating nausea and vomiting associated with chemotherapy, pain, as agents for stimulating appetite in AIDS patients suffering from the wasting syndrome and for treatment of glaucoma have prompted the present inventors to develop an ex vivo enzyme catalyzed semi-synthetic protocol for the large scale production of cannabinoids and cannabinoid analogs. The inventive methodologies also permit the synthesis of cannabinoids and their analogs at reduced costs.

SUMMARY OF THE INVENTION

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

In one of its aspects the present invention provides a method of producing a cannabinoid or a cannabinoid analog by:

(a) selecting a compound according to Formula I;

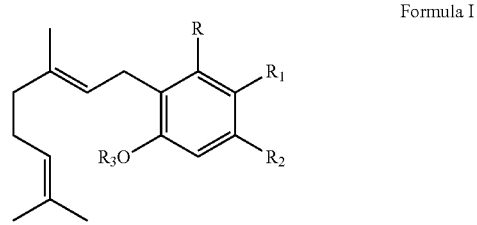

Formula I (b) selecting a cannabinoid synthase as a catalyst for transforming the Formula I compound to the cannabinoid or cannabinoid analog;
(c) contacting the Formula I compound with the cannabinoid synthase; and
(d) isolating the product from step (b). Pursuant to this synthetic strategy, the isolated product may be decarboxylated.

In Formula I, R is selected from —OH, halogen, —SH, or a —$NR_aR_b$ group. Substituents $R_1$ and $R_2$ are each independently selected from the group consisting of —H, —C(O)$R_a$, —O$R_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene.

For certain Formula I compounds, $R_1$ and $R_2$ together with the carbon atoms to which they are bonded form a $C_5$-$C_{10}$ cyclic ring. In one aspect, the $C_5$-$C_{10}$ cyclic ring comprises one or more heteroatoms selected from oxygen, sulfur or nitrogen. $R_3$ in Formula I is selected from the group consisting of H, —C(O)$R_a$ and $C_1$-$C_{10}$ linear or branched alkyl, while $R_a$ and $R_b$ are each independently —H, —OH, —SH, —$NH_2$, ($C_1$-$C_{10}$) linear or branched alkyl, or a $C_3$-$C_{10}$ cycloalkyl. The synthesis of tetrahydrocannabinol or cannabidiol, however, are not permitted by the inventive method.

Pursuant to this strategy, the cannabinoid synthase is selected from the group cannabidiolic acid synthase, a tetrahydrocannabinolic acid synthase or a cannabichromene acid synthase.

$R_2$ in Formula I can be a linear alkylene, a $C_2$-$C_{10}$ alkenylene, such as

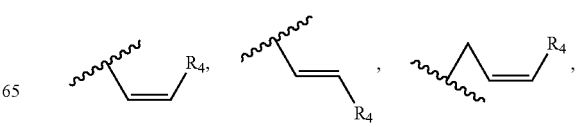

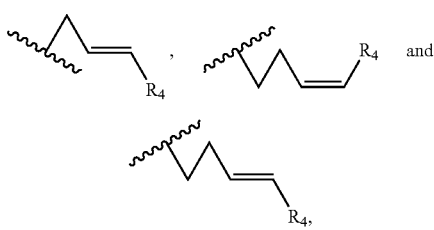

or a $C_2$-$C_{10}$ linear or branched alkynylene selected from

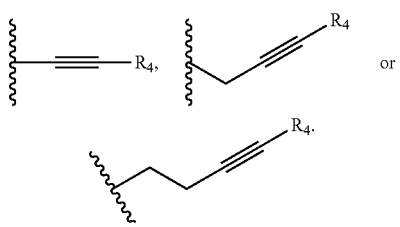

For certain Formula I compounds $R_2$ is

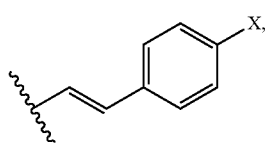

where X is selected from —OH, —SH, or —$NR_aR_b$.

In one of its aspects, the inventive method describes the immobilization of a cannabinoid synthase to a solid support. Cannabinoids and cannabinoid analogs produced according to the method described above exists as a single enantiomer. The enantiomeric purity of these compounds is from at least 95% to at least 99%.

According to another embodiment is provided a method of producing a cannabinoid or a cannabinoid analog according to Formula II, by:

(a) reacting a compound according to Formula III with a compound according to Formula IV;

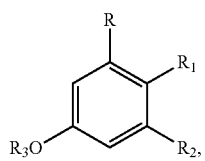

Formula III

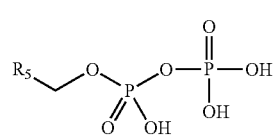

Formula IV in the presence of an enzyme that catalyzes the reaction of the Formula III and Formula IV compounds to form a Formula II compound;

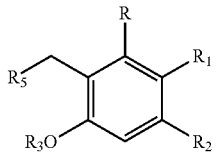

Formula II (b) contacting the Formula II compound with a cannabinoid synthase;

(c) isolating the product from step (b); and (d) optionally decarboxylating the product from (c) to obtain the cannabinoid or the cannabinoid analog.

Substituents R, $R_1$, $R_2$ and $R_3$ are as defined above and $R_5$ is selected from the group consisting of a linear or branched ($C_1$-$C_{10}$)alkylene, a linear or branched ($C_2$-$C_{10}$)alkenylene, a linear or branched ($C_2$-$C_{10}$)alkynylene, —C(O)— ($C_1$-$C_{10}$) alkylene, —C(O)—($C_2$-$C_{10}$)alkenylene and —C(O)—($C_2$-$C_{10}$)alkynylene. Furthermore, for Formulae II, III and IV compounds, any alkylene, alkenylene, alkynylene, aryl, arylalkylene, or cycloalkyl group is further substituted with one or more groups selected from the group consisting of —OH, halogen, —$NR_bR_c$, —C(O)$R_a$, —C(O)$NR_bR_c$, ($C_1$-$C_{10}$) alkyl, —CN, ($C_1$-$C_4$)alkoxy, ($C_1$-$C_4$)haloalkyl, and ($C_1$-$C_4$) hydroxyalkyl and $R_a$, $R_b$ and $R_c$ can each independently be —H, —OH, —SH, —$NH_2$, ($C_1$-$C_{10}$) linear or branched alkyl, or a $C_3$-$C_{10}$ cycloalkyl.

Also provided is a method for producing a tetrahydrocannabinol, cannabichrome, or both tetrahydrocannabinol and cannabichrome, or their analogs by:

(a) selecting a compound according to Formula V;

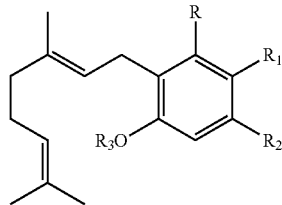

Formula V (b) contacting the Formula V compound with tetrahydrocannabinolic acid synthase;

(c) modifying at least one property of a reaction mixture comprising a Formula V compound and tetrahydrocannabinolic acid synthase to obtain a tetrahydrocannabinol, a cannabichromene, or both tetrahydrocannabinol and cannabichrome, or their analogs as products.

For Formula V compounds, R is selected from —OH, halogen, —SH, or a —$NR_aR_b$ group, $R_1$ and $R_2$ are each independently selected from the group consisting of —H, —C(O)$R_a$, —O$R_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$) aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene, and $R_3$ is selected from H, —C(O)$R_a$, or $C_1$-$C_{10}$ linear or branched alkyl. For certain compounds, $R_1$ and $R_2$ together with the carbon atoms to which they are bonded form a $C_5$-$C_{10}$ cyclic ring and substituent groups $R_a$ and $R_b$ are each independently —H, —OH, —SH, —$NH_2$, ($C_1$-$C_{10}$) linear or branched alkyl, or a $C_3$-$C_{10}$ cycloalkyl.

In one aspect, modifying at least one property of a reaction mixture comprises changing the pH of the reaction mixture, for example, changing the pH to be in the range from about 4.0 to about 8.0 units so as to control the ratio of tetrahydrocannabinol to cannabichrome produced by the above described method.

The present technology also provides a system for producing cannabinoids or cannabinoid analogs. Such a system comprises a fermentor holding a medium and a plurality of cells, wherein the cells are configured to produce and secrete cannabinoid synthase, a bioreactor containing a reactant, the reactant configured to interact with cannabinoid synthase to form a first cannabinoid and a second cannabinoid, and a control mechanism configured to control a condition of the bioreactor. The latter control mechanism is used to influence a quantity formed of the first cannabinoid relative to a quantity formed of a second cannabinoid.

The system may further comprise a filter configured to at least partially separate the plurality of cells from the medium, such that after separation the medium containing a cannabinoid synthase is introduced into a bioreactor. In one embodiment, the enzyme expressed by the plurality of cells includes a tag that permits the enzyme to bond to a nickel support within the bioreactor. Any Formula I compound or cannabigerolic acid can serve as the substrate for the enzyme tetrahydrocannabinoilic acid synthase. Depending on the conditions within the bioreactor, tetrahydrocannabinolic acid or cannabichromenic acid is produced as the first cannabinoid and the second cannabinoid will be the other of tetrahydrocannabinolic acid and cannabichromenic acid.

BRIEF DESCRIPTION OF THE DRAWINGS

FIG. 1 is a schematic illustration of a system for producing cannabinoids or cannabinoid analogs, according to an exemplary embodiment.

DETAILED DESCRIPTION OF THE PREFERRED EMBODIMENTS

Definitions

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "alkyl" refers to a straight or branched chain, saturated hydrocarbon having the indicated number of carbon atoms. For example, $(C_1-C_{10})$alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkenyl" refers to a straight or branched chain unsaturated hydrocarbon having the indicated number of carbon atoms and at least one double bond. Examples of a $(C_2-C_{10})$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" refers to a straight or branched chain unsaturated hydrocarbon having the indicated number of carbon atoms and at least one triple bond. Examples of a $(C_2-C_{10})$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" refers to an —O-alkyl group having the indicated number of carbon atoms. For example, a $(C_1-C_6)$ alkoxy group includes —O-methyl, —O-ethyl, —O-propyl, —O— isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 3- to 14-member monocyclic, bicyclic, tricyclic, or polycyclic aromatic hydrocarbon ring system. Examples of an aryl group include naphthyl, pyrenyl, and anthracyl. An aryl group can be unsubstituted or optionally substituted with one or more substituents as described herein below.

The terms "alkylene," "alkenylene," and "arylene," alone or as part of another substituent, means a divalent radical derived from an alkyl, cycloalkyl, alkenyl, aryl, or heteroaryl group, respectively, as exemplified by —CH$_2$CH$_2$CH$_2$CH$_2$—. For alkylene, alkenyl, or aryl linking groups, no orientation of the linking group is implied.

The term "halogen" and "halo" refers to —F, —Cl, —Br or —I.

The term "heteroatom" is meant to include oxygen (O), nitrogen (N), and sulfur (S).

A "hydroxyl" or "hydroxy" refers to an —OH group.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "cycloalkyl" refer to monocyclic, bicyclic, tricyclic, or polycyclic, 3- to 14-membered ring systems, which are either saturated, unsaturated or aromatic. The heterocycle may be attached via any heteroatom or carbon atom. Cycloalkyl include aryls and hetroaryls as defined above. Representative examples of cycloalky include, but are not limited to, cycloethyl, cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term 'nitrile or cyano" can be used interchangeably and refer to a —CN group which is bound to a carbon atom of a heteroaryl ring, aryl ring and a heterocycloalkyl ring.

The term "amine or amino" refers to an —NR$_c$R$_d$ group wherein R$_c$ and R$_d$ each independently refer to a hydrogen, $(C_1-C_8)$alkyl, aryl, heteroaryl, heterocycloalkyl, $(C_1-C_8)$haloalkyl, and $(C_1-C_6)$hydroxyalkyl group.

The term "alkylaryl" refers to $C_1-C_8$ alkyl group in which at least one hydrogen atom of the $C_1-C_8$ alkyl chain is replaced by an aryl atom, which may be optionally substituted with one or more substituents as described herein below. Examples of alkylaryl groups include, but are not limited to, methylphenyl, ethylnaphthyl, propylphenyl, and butylphenyl groups.

"Arylalkylene" refers to a divalent alkylene wherein one or more hydrogen atoms in the $C_1$-$C_{10}$ alkylene group is replaced by a ($C_3$-$C_{14}$)aryl group. Examples of ($C_3$-$C_{14}$)aryl-($C_1$-$C_{10}$)alkylene groups include without limitation 1-phenylbutylene, phenyl-2-butylene, 1-phenyl-2-methylpropylene, phenylmethylene, phenylpropylene, and naphthylethylene.

"Arylalkenylene" refers to a divalent alkenylene wherein one or more hydrogen atoms in the $C_2$-$C_{10}$ alkenylene group is replaced by a ($C_3$-$C_{14}$)aryl group.

The term "arylalkynylene" refers to a divalent alkynylene wherein one or more hydrogen atoms in the $C_2$-$C_{10}$ alkynylene group is replaced by a ($C_3$-$C_{14}$)aryl group.

The terms "carboxyl" and "carboxylate" include such moieties as may be represented by the general formulas:

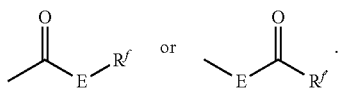

E in the formula is a bond or O and $R^f$ individually is H, alkyl, alkenyl, aryl, or a pharmaceutically acceptable salt. Where E is O, and $R^f$ is as defined above, the moiety is referred to herein as a carboxyl group, and particularly when $R^f$ is a hydrogen, the formula represents a "carboxylic acid". In general, where the expressly shown oxygen is replaced by sulfur, the formula represents a "thiocarbonyl" group.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

The present invention focuses on methodologies for enzyme catalyzed synthesis of cannabinoids or cannabinoid analogs in a cell-free environment. Also described is an apparatus for the ex vivo manufacture of cannabinoids and analogs of cannabinoids. The term "analog" refers to a compound that is structurally related to naturally occurring cannabinoids, but whose chemical and biological properties may differ from naturally occurring cannabinoids. In the present context, analog or analogs refer compounds that may not exhibit one or more unwanted side effects of a naturally occurring cannabinoid. Analog also refers to a compound that is derived from a naturally occurring cannabinoid by chemical, biological or a semi-synthetic transformation of the naturally occurring cannabinoid.

Illustrative of cannabinoid compounds included in the inventions and without limitation are cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide and nabilone, as well as natural or synthetic molecules that have a basic cannabinoid structure and are modified synthetically to provide a cannabinoid analog.

The present technology also relates to the large scale cloning and expression of the enzymes that play a role in the biosynthesis of cannabinoids and the use of an eukaryotic expression system for the manufacture of cannabinoids and cannabinoid analogs. Exemplary of eukaryotic cells suitable for cloning and expression of the cannabinoid synthase enzymes include without limitation *E coli*, yeast and baculovirus hosts. In an embodiment of this technology, is disclosed a method for the large-scale production of several cannabinoid synthase enzymes including tetrahydrocannabinolic acid synthase (THCA synthase), cannabichromenic acid synthase (CBCA synthase) and cannabidiolic acid synthase (CBDA synthase) using the pink *Pichia* yeast expression system. Accordingly, the large scale production of these enzymes can be carried out by transforming yeast with a DNA construct that comprises a gene for THCA synthase, CBCA synthase, or CBDA synthase, and culturing the transformed yeast cells under conditions suitable for promoting the expression of a functionally active enzyme.

The sequences for the genes for THCA synthase and CBDA synthase were obtained from a publicly available database and their protein coding regions were altered to optimize protein expression in *Pichia Pastoris* yeast cells. Codon optimization was carried out using the GeneArt® program from Invitrogen.

Additionally, both genes were modified to include the yeast alpha secretory sequence as well as codons for the inclusion of a His-tag in the expressed protein. The former was inserted at the 5'-end of the gene and is necessary for the extracellular secretion of the expressed protein. Codons for the His-tag are present at the 3'-end of the gene and are introduced to facilitate the purification of the expressed protein by affinity chromatography.

These chimeric sequences, alpha-CBDA synthase and alpha-THCA synthase, were inserted into pPink-HC vector (Invitrogen®), and were used to obtain Top 10 F⁻ transformed *E. coli* cells which were stored as agar stabs for future use. Prior to transformation of yeast cells, the vector containing the cannabinoid synthase gene of interest (GOI) was isolated from agar stabs containing transformed *E. coli* cells, and linearized using PmeI or SpeI restriction enzymes. The linearized plasmids were electroporated into *Pichia pastoris* pepB deficient mutant cells using PichiaPink™ Yeast Expression Systems (Invitrogen®). Linearization using the restriction enzyme PmeI directs the insert into the AOX1 promoter region of the *pichia* genome, while the restriction enzyme SpeI directs the insert into the TRP gene.

The transformed yeast cells were grown on adenine-deficient selective plates and a color-based screen was used to identify positive transformants. Pursuant to this screening methodology, red/pink colonies signal transformants that do not carry the gene of interest as well as transformants carrying a limited number of copies of the gene of interest integrated into the genome of *Pichia pastoris*. White colonies on the other hand, indicate transformants having multiple copies of the gene of interest. Typically, cells having 6-10 copies of the gene of interest are desired for obtaining large amounts of recombinant protein, for example, about 1.0 g to about 2.0 g of protein per liter of culture. An enzyme assay that quantitated the conversion of substrate cannabigerolic acid (CBGA) to THCA or CBDA products upon induction of THCA synthase or CBDA synthase by the addition of methanol to transformed yeast cells was used to identify white colonies of yeast cells that produced greater than 20% conversion of substrate to product.

Accordingly, individual white colonies of yeast cells carrying the THCA synthase gene or the CBDA synthase gene were separately cultured in flasks using BMGY medium, followed by induction by growth in BMMY medium, to induce the expression of THCA synthase or CBDA synthase as further described below. Briefly, the medium containing the enzyme in each culture was separated from the cells and a known amount of the substrate CBGA was added to the medium from each culture flask. Following incubation, each culture flask was analyzed to quantitate the percent conversion of CBGA to product. Cultures of transformants showing greater than 20% conversion will be used for the commercial synthesis of cannabinoids or cannabinoid analogs pursuant to methodologies of the invention.

The cannabinoid synthase enzymes, THCA synthase and CBDA synthase, obtained using the PichiaPink™ Yeast Expression system described above, can be used for the manufacture of cannabinoids or an analog of a cannabinoid. In one embodiment is provided a method for producing a cannabinoid or a cannabinoid analog by selecting a Formula I compound and a cannabinoid synthase as a catalyst for transforming the Formula I compound to a cannabinoid or a cannabinoid analog.

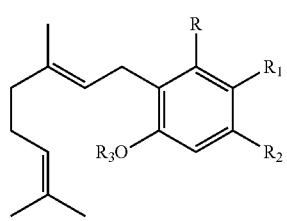

Formula I

In Formula I, R can be selected from hydroxyl (—OH), halogen, thiol (—SH), or a —NR$_a$R$_b$ group. Substituent groups R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$) aryl-(C$_2$-C$_{10}$)alkenylene, and (C$_3$-C$_{10}$)aryl-(C$_1$-C$_{10}$)alkynylene. Alternatively, R$_1$ and R$_2$ together with the carbon atoms to which they are bonded form a C$_5$-C$_{10}$ cyclic ring. For compounds according to Formula I, R$_3$ is selected from the group consisting of H, —C(O)R$_a$ and C$_1$-C$_{10}$ linear or branched alkyl and R$_a$ and R$_b$ are each independently —H, —OH, (C$_1$-C$_{10}$) linear or branched alkyl, —SH, —NH$_2$, or a C$_3$-C$_{10}$ cycloalkyl.

The cannabinoid or cannabinoid analog obtained by contacting a Formula I compound with a cannabinoid synthase can be isolated, purified and used as a therapeutic or and the cannabinoid or cannabinoid analog can undergo an optional decarboxylation step to convert, for example, cannabichromenic acid (CBCA) to cannabichromene (CBC) prior to the latter's use as a pharmaceutical agent or a nutraceutical agent.

For certain embodiments the cannabinoid synthase is cannabidiolic acid synthase. For other aspects of this technology, the cannabinoid synthase is tetrahydrocannabinolic acid synthase or a cannabichromene acid synthase. For certain Formula I compounds R$_1$ and R$_2$ together with the ring carbon atoms to which they are bonded form a C$_5$-C$_{10}$ cyclic ring. For such Formula I compounds one or more carbon atoms of the ring can be substituted with a heteroatom selected from oxygen, sulfur or nitrogen.

For compounds according to Formula I, R$_2$ can be a linear alkylene or a branched alkylene. Exemplary of linear alkylenes include without limitation CH$_3$, C$_2$H$_5$, C$_3$H$_7$, C$_4$H$_9$, C$_5$H$_{11}$, C$_6$H$_{13}$, C$_7$H$_{15}$ and C$_8$H$_{17}$. Illustrative of branched alkylenes are groups selected from, isopropyl, sec-butyl, isobutyl, neopentyl, 2-methyl hexyl, or 2,3-dimethyl hexyl groups. In some embodiments, R$_2$ can be an optionally substituted linear or branched alkylene in which one or more hydrogen atoms is replaced without limitation with a group selected from chlorine, fluorine, bromine, nitro, amino, hydroxyl, phenyl, or benzyl group.

For certain Formula I compounds R$_2$ is a C$_2$-C$_{10}$ alkenylene and is selected from the group consisting of

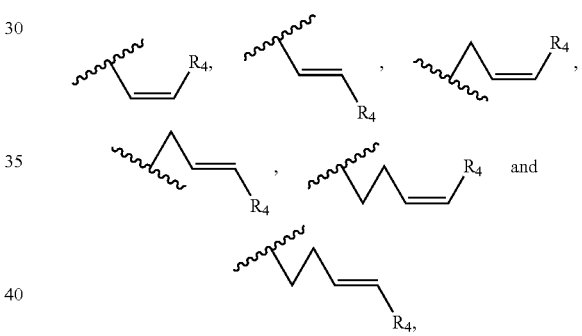

with R$_4$ being a linear or branched alkylene as described above. When R$_2$ is a C$_2$-C$_{10}$ linear or branched alkynylene, R$_2$ can be

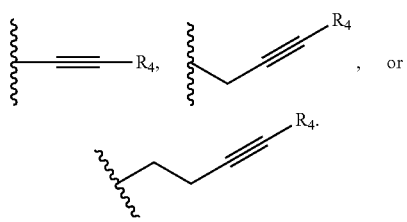

Alternatively, R$_2$ in Formula I is

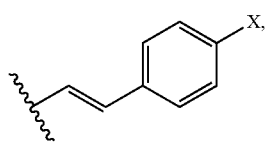

substituent X is a group selected from —OH, —SH, or $NR_aR_b$ and groups $R_a$ and $R_b$ are as defined above.

Many of the naturally occurring cannabinoids are produced as their carboxylic acid derivatives in plants. Their psychostimulatory activity is enhanced, however, following decarboxylation which occurs upon the application of heat to the cannabinoid acid containing plant tissue or by drying the plant material prior to use. Cannabinoid and cannabinoid analogs synthesized using the inventive method can also have a carboxylic acid (—COOH) group as the $R_1$ substituent and such compounds may undergo an optional decarboxylation step prior to their use as pharmaceutical or nutraceutical agents. Exemplary of such a cannabinoid or cannabinoid analog is the compound obtained by contacting a Formula I species in which R is —OH, $R_1$ is —COOH, $R_2$ is $C_5H_{11}$ and $R_3$ is —H with a cannabinoid synthase.

The synthesis, isolation and purification of cannabinoids or cannabinoid analogs can be improved by immobilization of a cannabinoid synthase to a solid support, or by encapsulation of the synthase within a liposome. In one aspect of the synthesis, the enzyme is immobilized to a solid support. Such immobilization is advantageous, since it permits recycling and reuse of the immobilized enzyme which significantly reduces the costs associated with the manufacture of pharmaceutical grade cannabinoids or cannabinoid analogs. Immobilization of the enzyme also permits ease of use and recovery of the enzyme catalyst, ease of purification of the desired product, preservation of the enantiomeric excess (ee) of the final product and an overall improvement in the yield of the product. Typically, the enantiomeric purity of a cannabinoid or a cannabinoid analog according to the claimed method is from about 90% ee to about 100% ee, for instance, a cannabinoid or a cannabinoid analog produced using the inventive methodology can have an enantiomeric purity of about 91% ee, about 92% ee, about 93% ee, about 94% ee, about 95% ee, about 96% ee, about 97% ee, about 98% ee and about 99% ee.

Typically, the enzyme to be immobilized can be absorbed onto a solid support, adsorbed onto a support, covalently linked to a support or can be immobilized onto a solid support through ionic interactions. In one embodiment, the cannabinoid synthase is covalently linked to a solid support. Suitable strategies for linking an enzyme to a solid support are well known in the biochemical art and include covalent linkages between an appropriately functionalized support and a side chain of an amino acid group or through covalent linkages using appropriately functionalized linkers or spacers to separate the support from the enzyme. The term "linker" refers to any group that separates the support from the enzyme. Accordingly, a linker is a group that is covalently tethered at one end to a group on the surface of the support and is attached to the enzyme at the other end. Illustrative linkers include $(C_1-C_{10})$alkylene linker polymers of ethylene glycol such as a —$(OCH_2—CH_2)_n$—O— group, where n is an integer from 0 to 10, —$(C_1-C_{10})$alkylene-NH—, —$(C_1-C_{10})$alkylenesiloxy, or a —$(C_1-C_{10})$alkylene-C(O)—.

Supports suitable for immobilizing enzymes include without limitation Ameberlite resins, Duolite resins, acrylic resins such as Eupergit® C, DEAE-Sephadex and gels made using polyvinyl alcohol can be used as supports for immobilizing the cannabinoid synthase enzymes of the present technology.

Cannabinoids exert different physiological properties and are known to lessen pain, stimulate appetite and have been tested as candidate therapeutics for treating a variety of disease conditions such as allergies, inflammation, infection, epilepsy, depression, migraine, bipolar disorders, anxiety disorder, and glaucoma. The physiological effect exerted by a cannabinoid depends in large part to its ability to stimulate or deactivate the cannabinoid receptors, for instance the CB1, CB2 and CB3 receptors. Since modulation of receptor activity depends on the binding interactions and the orientation of a ligand within the cannabinoid receptors active site, it follows that the nature and orientation of substituent groups attached to a cannabinoid or a cannabinoid analog will affect the pharmaceutical properties exhibited by such compounds.

In one embodiment is provided a method for the manufacture cannabinoids having structurally distinct and diverse substituent groups attached to a central core. Such compounds are expected to exhibit different pharmaceutically beneficial properties. Structural diversity will be introduced by contacting an appropriately substituted Formula III compound with a Formula IV compound in the presence of an enzyme, such as GPP olivetolate geranyltransferase (a polyketide synthase), to give a Formula II compound. Scheme 1 structurally illustrates the protocol for synthesizing a Formula II compound pursuant to this embodiment.

Scheme 1

Depending on the nature and type of substituent groups at R, $R_1$, $R_2$, $R_3$ and $R_5$, in Formulae III and IV, the inventive method permits the synthesis of Formula II compounds having different substituent groups surrounding the central phenyl core as precursors or synthons for the manufacture of a cannabinoid or a cannabinoid analog. According to this method, therefore, the cannabinoid or cannabinoid analogs can be obtained by contacting a Formula II compound with a cannabinoid synthase, for example, THCA synthase, CBCA synthase or a CBDA synthase, followed by isolation and decarboxylation of the obtained product to give a cannabinoid or a cannabinoid analog.

In Formula III, R can be selected from hydroxyl (—OH), halogen, thiol (—SH), or a —$NR_aR_b$ group. Substituents $R_1$ and $R_2$ are each independently selected from the group consisting of —H, —$C(O)R_a$, —$OR_a$, an optionally substituted linear or branched $(C_1-C_{10})$alkylene, an optionally substituted linear or branched $(C_2-C_{10})$alkenylene, an optionally substituted linear or branched $(C_2-C_{10})$alkynylene, an optionally substituted $C_3-C_{10}$ aryl, an optionally substituted $C_3-C_{10}$ cycloalkyl, $(C_3-C_{10})$aryl-$(C_1-C_{10})$alkylene, $(C_3-C_{10})$aryl-$(C_2-C_{10})$alkenylene, and $(C_3-C_{10})$aryl-$(C_1-C_{10})$alkynylene.

In certain embodiments $R_1$ and $R_2$ together with the carbon atoms to which they are bonded form a $C_5-C_{10}$ cyclic ring and $R_3$ is selected from the group consisting of H, —C(O)$R_a$ and $C_1$-$C_{10}$ linear or branched alkyl.

$R_5$ in Formula IV can be a linear or branched ($C_1$-$C_{10}$) alkylene, a linear or branched ($C_2$-$C_{10}$)alkenylene, a linear or branched ($C_2$-$C_{10}$)alkynylene, —C(O)—($C_1$-$C_{10}$)alkylene, —C(O)—($C_2$-$C_{10}$)alkenylene and —C(O)—($C_2$-$C_{10}$)alkynylene. For Formulae II, III and IV compounds any alkylene, alkenylene, alkynylene, aryl, arylalkylene, or cycloalkyl group can be further substituted with one or more groups selected from the group consisting of —OH, halogen, —$NR_b$$R_c$, —C(O)$R_a$, —C(O)$NR_b$$R_c$, ($C_1$-$C_{10}$)alkyl, —CN, ($C_1$-$C_4$) alkoxy, ($C_1$-$C_4$)haloalkyl, and ($C_1$-$C_4$)hydroxyalkyl with $R_a$, $R_b$ and $R_c$ each independently being selected from —H, —OH, or ($C_1$-$C_{10}$) linear or branched alkyl, —SH, —$NH_2$, or a $C_3$-$C_{10}$ cycloalkyl.

According to one embodiment, $R_5$ in Formula IV can be a ($C_2$-$C_{10}$)alkenylene selected from

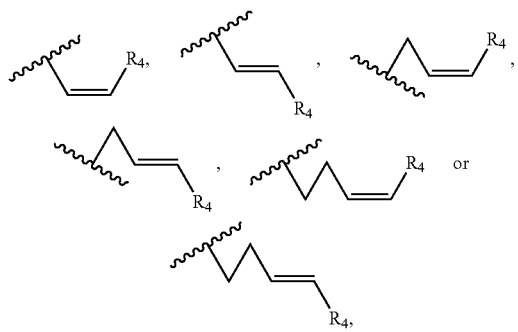

with $R_4$ being a linear alkylene selected from the group consisting of $CH_3$, $C_2H_5$, $C_3H_7$, $C_4H_9$, $C_5H_{11}$, $C_6H_{13}$, $C_7H_{15}$ and $C_8H_{17}$. For certain Formula IV compounds $R_5$ is

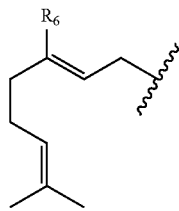

and group $R_6$ is selected from ($C_1$-$C_{10}$)alkylene, ($C_2$-$C_{10}$) alkenylene, —OH, —SH, $NO_2$, F, Cl, Br, —$NH_2$, or a —$NHR_a$ where $R_a$ is as defined above.

Enzymes are very specific with respect to the type of chemical reactions they catalyze and the nature and type of substrates that are involved in these reactions. Enzymes also exhibit a high level of stereospecificity, regiospecificity and chemoselectivity. It was therefore unexpected, when the present inventors observed that the enzyme THCA synthase could produce two different products, tetrahydrocannabinolic acid (THCA) and cannabichromenic acid (CBCA) using the same substrate cannabigerolic acid (CBGA), depending on the conditions under which the cyclization reaction is catalyzed.

Accordingly, the effects of temperature, pH, solvent, ionic strength and incubation times on the distribution ratio of THCA to CBCA products were studied. In one embodiment, the effect of solvent on product distribution ratio was evaluated. Cannabinoids are lipohilic in nature and are poorly solubilized in aqueous solvents. The poor solubility of cannabinoids in aqueous solvent has prevented the development of ex-vivo enzyme catalyzed methodologies for the synthesis of cannabinoids and cannabinoid analogs. The present inventors surprisingly found that THCA synthase retained its catalytic activity in a solvent mixture containing buffer and a non-aqueous solvent, such as dimethyl sulfoxide (DMSO), dimethyl formamide (DMF), iso-propoyl alcohol and cyclodextrin if the concentration of non-aqueous solvent in the mixture was maintained below 40% v/v.

For instance, enzyme catalysis was most effective when the concentration of the non-aqueous solvent was about 20%. The catalytic rate decreases slightly as concentration of the non-aqueous solvent is increased. Thus, 20% DMSO gave the highest catalytic rate, approximately 2.5-fold faster than catalysis in buffer alone. Table 1 illustrates the effect of concentration of non-aqueous solvent on the rate of catalytic activity.

As further illustrated in this table, the concentration of non-aqueous solvent can alter the ratio of THCA to CBCA produced as product. Thus, greater levels of THCA are obtained when the concentration of DMSO in buffer is less that 20%, with a THCA:CBCA distribution ratio of 10:1 observed when 10% DMSO is used as the solvent.

TABLE 1

| DMSO | FASTER | THCA:CBCA |
|---|---|---|
| 0% | 1X | |
| 10% | 1.2X | 10:1 |
| 20% | 2.5X | 5:1 |
| 25% | — | 1:1 |
| 30% | 0.3X | |

It was observed that the addition of a detergent such as sodium dodecyl sulfate (SDS), to a 100 mM sodium phosphate buffer did not impact the percent conversion of substrate CBGA to product. In contrast, addition of SDS to 100 mM citrate buffer containing cyclodextrin destroyed THCA synthases ability to catalyze reaction. Only 8% of the substrate was converted to product under these reaction conditions with the formation of THCA being favored as product under these reaction conditions.

Cannabigerolic acid (CBGA) serves as a common substrate for different cannabinoid synthase enzymes during the biosynthesis of naturally occurring cannabinoids. For instance, previous studies have suggested that the enzymes THCA synthase, CBDA synthase and CBCA synthase to each use CBGA as their substrate during the biosynthesis of tetrahydrocannabinolic acid, cannabidiolic acid and cannabichromenic acid respectively.

Thus, during a study aimed at evaluating the optimal pH for THCA synthase activity, the present inventors were surprised to note that depending on the pH at which catalysis was carried out the enzyme THCA synthase catalyzed the conversion of substrate CBGA to either THCA or CBCA. This observation was unexpected since a single enzyme THCA synthase, could be responsible for the formation of two different cannabinoid products in plants.

Table 3 illustrates the results of a pH study that was aimed at identifying the effect of pH on product ratio, namely, the ratio of THCA to CBCA compounds produced when THCA synthase is contacted with CBGA as substrate. The pH of the reaction mixture in this study ranged from a pH of 4.0 to 8.0. Higher pH values were not tested since THCA synthase is catalytically inactive at a pH greater than 8.0.

As illustrated in Table 3, THCA is preferentially synthesized at pH values less than 6.0. In fact, THCA is the major product when catalysis is carried out at a pH of 4.0. Increasing the pH of the reaction mixture altered the product distribution ratio with approximately 30% CBCA being produced as product at a pH of 5.0 and around 15% CBCA being produced as product at a pH value of 6.0. A further increase in pH of the reaction mixture, such as an increase of the pH of the reaction mixture to a pH of 7.0 gave CBCA exclusively as the product of THCA synthase catalyzed conversion of CBGA. Any further increases in pH, moreover, reduced or eliminated catalytic activity of THCA synthase, with no product observed for a reaction mixture at a pH of 8.0.

TABLE 3

| pH | THCA | CBCA |
|----|------|------|
| 4  | 100  | Trace |
| 5  | 70   | 30   |
| 6  | 85   | 15   |
| 7  | 0    | 100  |
| 8  | 0    | 0    |

Accordingly, in one embodiment the invention provides a method for producing a tetrahydrocannabinol, cannabichrome or both tetrahydrocannabinol and cannabichrome, or their analogs by selecting a Formula V compound as a reactant, contacting the Formula V compound with tetrahydrocannabinolic acid synthase (THCA synthase) and modifying at least one property of the reaction mixture to obtain tetrahydrocannabinol, cannabichrome or both tetrahydrocannabinol and cannabichrome, or their analogs as products.

In Formula V, R is selected from —OH, halogen, —SH, or a —$NR_aR_b$ group. Substituents $R_1$ and $R_2$ are each independently selected from the group consisting of —H, —$C(O)R_a$, —$OR_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene.

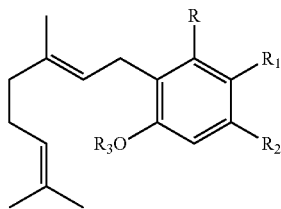

Formula V

For certain embodiments, $R_1$ and $R_2$ together with the ring carbon atoms to which they are bonded form a $C_5$-$C_{10}$ cyclic ring in which one or more carbon atoms can optionally be replaced with one or more heteroatoms selected from oxygen, sulfur, nitrogen or a —$NR^a$ group. $R_3$ in Formula V, can be a group selected from H, —$C(O)R_a$ or a ($C_1$-$C_{10}$) linear or branched alkyl and substituents $R_a$ and $R_b$ are each independently selected from —H, —OH, —SH, $NH_2$, ($C_1$-$C_{10}$) linear or branched alkyl, or a $C_3$-$C_{10}$ cycloalkyl moiety.

Any physical property known to have an effect on enzyme activity and catalysis can be modulated to alter the ratio of the products THCA to CBCA. In one embodiment, therefore, the pH of the reaction mixture was changed to modulate the ratio of THCA to CBCA produced enzymatically as products.

Pursuant to this synthetic methodology, catalysis at a lower pH in the range from about 4.0 to about 6.0 favored the formation of THCA as product while catalysis at a neural pH in the range from about 6.5 to about 7.5 favored the formation of CBCA as product.

Thus, the present inventors have shown that it is possible to control the formation of THCA or CBCA as the product of catalysis by controlling the pH of the reaction mixture.

Other physical properties such as the compositional makeup of the reaction solvent, ionic strength, temperature, pressure, viscosity of the reaction medium and concentration of reagents can also alter product ratio. Many of these physical parameters, in fact, play an important role in modulating catalysis during the large scale manufacture of cannabinoids or cannabinoid analogs using a bioreactor.

Thus, in one embodiment is provided a system (100) for producing a cannabinoid or a cannabinoid analog by controlling a condition that influences the quantity of a first cannabinoid or its analog formed in relation to the quantity of a second cannabinoid or its analog. The system (100), shown schematically in FIG. 1, may comprise a fermentor (2), a filter (18), a bioreactor (10), and a control mechanism (20). A description of the System as represented in FIG. 1 is provided below.

The fermentor (2) holds cell culture medium (4) and a plurality of cells (6). The cells (6) are configured to produce and secrete a cannabinoid synthase (8). The cells (6) used in the fermentor (2) for the manufacture of a cannabinoid synthase (8) can be any eukaryotic cell that has been genetically modified to include a nucleic acid sequence or a gene that encodes a cannabinoid synthase protein. In certain embodiments, the nucleic acid sequence that encodes a cannabinoid synthase protein is modified to include an yeast alpha secretion sequence at its 5' end and to incorporate a 6-residue histidine tag at its 3' end. The addition of the yeast alpha secretion sequence permits secretion of the cannabinoid synthase protein into the medium used for eukaryotic cell growth. The extracellular secretion of the cannabinoid synthase (8) is advantageous, since it facilitates the separation and transport of the enzyme between the fermentor (2) and the bioreactor (10) using the filter (18). Following production of cannabinoid synthase (8) in the fermentor (2), the supernatant (e.g. medium (4), cells (6), and cannabinoid synthase (8) is transported along path (24) to the filter (18). Path (24) may be a pipe or any other pathway suitable for transporting the supernatant.

The filter (18) may filter the supernatant to at least partially separate the cells (6) from the medium (4) containing the expressed enzyme. Typically, the filter (18) separates at least 80% of the total cells (6) from the medium (4). For certain embodiments, the filter (18) separates at least 85%, at least 90%, at least 91%, at least 92%, at least 93%, at least 94%, at least 95%, at least 96%, at least 97%, at least 98%, at least 99%, or 100% of the total cells (6) from the medium (4) prior to the introduction of this medium (4) into the bioreactor (10). Following filtration, the cells (6) are transported back to the fermentor (2) along path (26). In one embodiment, the filter (18) can be a filtration and purification system that includes multiple filters and reservoirs to purify the cannabinoid synthase (8).

After passing through the filter (18), the cannabinoid synthase (8) flows into the bioreactor (10) along path (28) and enters the bioreactor (10) through inlet (30). The bioreactor (10) also includes an inlet (32) for reactants, such as the substrate CBGA or other substrates according to the Formula I compound described above. Thus, as shown in FIG. 1, the bioreactor (10) contains a reactant (12) that is configured to interact with cannabinoid synthase (8) to form a first cannabinoid (14). The bioreactor (10) may also provide the environment for synthesis of a second cannabinoid (16). The second cannabinoid (16) may be produced using the same type of cannabinoid synthase (8) and a substrate as the first cannabinoid (14). For example, both the first cannabinoid (14) and the second cannabinoid (16) may be produced using CBGA as reactant (12) and THCA synthase as the cannabinoid synthase (8). In this embodiment, the first cannabinoid (14) may be THCA and the second cannabinoid (16) may be CBCA. In an alternative embodiment, the second cannabinoid (16) may be synthesized using a substrate or cannabinoid synthase different from those used in synthesis of the first cannabinoid (14).

The bioreactor (10) can be a column bioreactor having a solid support that is impregnated with divalent metal ions or a support whose surface is functionalized with divalent metal ions. Typically, sepharose, agarose or other biopolymers are used as supports for binding divalent metal ions such as nickel, cobalt, magnesium and manganese. Such supports have a strong affinity for the histidine tag that is present on the expressed cannabinoid synthase (8) and can be used to sequester the synthase and separate it from other non-essential proteins and debris that may interfere or impede cannabinoid synthesis.

The bioreactor (10) used for synthesizing cannabinoids is configured for batch and continuous synthetic processes to permit commercial production of pharmaceutically useful cannabinoids. In one embodiment, the bioreactor (10) is configured for batch synthesis in which the composition of the medium (4), concentration of the enzyme and substrate are fixed at the beginning of the process and not allowed to change during catalysis. Synthesis is terminated when the concentration of the desired product in the medium of the bioreactor (10) reaches a predetermined value or the concentration of substrate falls below a predetermined level, such as to a level where there is no detectable catalytic conversion of substrate to product.

In one embodiment, therefore, the His-tagged cannabinoid synthase (8) is sequestered onto a nickel containing resin support within the bioreactor column prior to the introduction of a known amount of substrate, for example, cannabigerolic acid (CBGA), or a Formulae I, II or V compound into the bioreactor (10). In an alternate embodiment, cannabigerolic acid (CBGA), or a Formulae I, II or V compound can be present within the bioreactor (10) having a nickel resin support prior to the introduction of the medium (4) containing a cannabinoid synthase (8) into the bioreactor (10). In either case, a known amount of the enzyme is contacted with a known amount of a Formulae I, II or V compound or CBGA as substrate to synthesize a cannabinoid or a cannabinoid analog as product, such as the first cannabinoid (14) or the second cannabinoid (16).

The progress of the reaction within the bioreactor (10) can be monitored periodically or continuously. For instance, an optical monitoring system may be utilized to detect the concentration of product in the medium (4) within the bioreactor (10) as a function of time. Alternatively, the decrease in the concentration of substrate can be monitored to signal termination of synthesis. The cannabinoid product thus produced can be readily recovered from the medium using standard solvent extraction or chromatographic purification methods. The monitoring system may be part of or may interact with the control mechanism (20), described further below.

An alternative to the batch process mode is the continuous process mode in which a defined amount of substrate and medium (4) are continuously added to the bioreactor (10) while an equal amount of medium (4) containing the cannabinoid product is simultaneously removed from the bioreactor (10) to maintain a constant rate for formation of product. Medium (4) can enter the bioreactor (10) through inlet (32) and exit the bioreactor (10) through outlet (34). Methods of modulating the concentration of substrate, enzyme and other factors implicated to maximize the rate of product formation are known in the art.

The conditions of the bioreactor (10) can be controlled using a control mechanism (20). The control mechanism (20) may be coupled to the bioreactor (10) or, alternatively, may interact with the bioreactor (10) wirelessly or remotely. The control mechanism (20) can control at least one condition of the bioreactor (10) so as to influence a quantity formed of the first cannabinoid (14) relative to a quantity formed of a second cannabinoid (16). For example, in one embodiment, the cannabinoid synthase (8) is THCA synthase and is produced by genetically engineered Pichia pastoris yeast cells. As described above, contact of this enzyme with cannabigerolic acid permits the production of both THCA or CBCA. One condition that influences the quantity of THCA produced relative to CBCA (e.g. the ratio of THCA to CBCA) is the pH of the medium (4) in the bioreactor (10). Other conditions within the bioreactor (10) may also influence the relative quantities of a first cannabinoid (14) (e.g. THCA) and second cannabinoid (16) (e.g. CBCA) produced in the bioreactor (10), such as temperature, pressure, and flow rate. In one embodiment, a change in condition (e.g. pH, temperature, pressure, and/or flow rate) can cause a shift from formation of the first cannabinoid (14) in greater quantities relative to the second cannabinoid (16) to formation of the second cannabinoid (16) in greater quantities relative to the first cannabinoid (14).

In another embodiment, the control mechanism (20) can also be used to control the conditions of the fermentor (2), such the oxygen level, agitation, pH, and feed rate. The control mechanism (20) may also control the flow of materials (e.g. by controlling pumps) into and out of the fermentor (2), filter (18), and bioreactor (10).

The control mechanism (20) can include a processing circuit having a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application, such as controlling the pH, temperature, and pressure of the bioreactor (10), or altering the flow rate of medium (4) into or out of the bioreactor (10). The memory device may be or include volatile memory or non-volatile memory. The memory device may include database components, object code components, script components, or any other type of information structure for supporting the various activities and information structures described in the present application. According to one embodiment, the memory device is communicably connected to the processor via the processing circuit and includes computer code for executing (e.g., by the processing circuit and/or processor) one or more processes described herein.

The present disclosure contemplates methods, systems and program products on any machine-readable media for accomplishing various operations, such as controlling the conditions of the bioreactor (10). The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The control mechanism (20) may further include additional devices, such as a keyboard (22) and display (36), to allow a user to interact with the control mechanism (20) to control the conditions of bioreactor (10). For example, the display may include a screen to allow a user to monitor changes in pH, temperature, pressure, and flow rate of the bioreactor (10), or to monitor any other condition of the system for producing cannabinoids or cannabinoid analogs.

The construction and arrangement of the system for producing cannabinoids or cannabinoid analogs as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. Furthermore, the order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present technology is further described by the following examples which are not meant to limit the scope of the claims.

EXAMPLES

A. Molecular Cloning, Screening and Expression of Protein from High Yield Yeast Transformants 1. Restriction Digestion.

THCA α plasmid DNA or CBDA a plasmid DNA were linearized by digesting the plasmid with Pme I or Spe I restriction enzymes at 37° C. for the appropriate time. The DNA was then ethanol precipitated using a 1:10 diluted solution of 3M sodium acetate and 2.5 volumes of 90% ethanol. After precipitation the DNA was pelleted by centrifuging at 12,000 rpm for 10 minutes. The pellet was washed with 804 of 80% ethanol and centrifuged to dryness using a heated centrifuge. This washing and centrifugation step was repeated and the DNA thus obtained was resuspended in 104 of sterile water and frozen at −20° C. prior to use.

2. Preparation of Electrocompetent Yeast Cells.

Electrocompetent PichiaPink (pPink) cells were made by inoculating 10 mL of YPD media with a glycerol stock of a genetically engineered Ade2, pep4 knockout pPink yeast strain 2. These cells were grown overnight in a 125 mL baffled flask at 27° C., using a shaker spinning at 270 rpm until the $OD_{600}$ of the culture reaches a value of 1.3 units indicating log phase growth. This culture was then added to 100 mL of YPD media and allowed to incubate overnight under the same conditions. The $OD_{600}$ was checked hourly and after a 12 hour incubation period reached a value of 1.3 units.

At this time, the culture was transferred to a 500 mL centrifuge tube and spun for 5 minutes at 4° C. and 5200 rpm. The supernatant was decanted and 250 mL of sterile ice cold water was added to resuspend the cells. This wash and centrifugation protocol was repeated twice to ensure complete removal of the YPD medium. A final wash was carried out using 50 mL of sterile ice cold water to suspend the cells followed by repelleting of the cells at 5200 rpm and removal of the supernatant by decantation.

To the cell pellet was added 10 mL of sterile ice cold 1M sorbitol. The sorbitol-cell mixture was then transferred to a sterile 15 mL conical tube and centrifuged at 5200 rpm. A second wash of the cell pellet using 300 µL of sterile ice cold 1M sorbitol was performed prior to using these cells for electroporation.

3. Electroporation.

The previously frozen linearized THCA α plasmid DNA or CBDA a plasmid DNA was thawed on ice and 80 µL of the electrocompetent pPink cells were added to the tube. This mixture was then transferred to a 0.2 cm electroporation cuvette and incubated on ice for 5 minutes. The cuvette was pulsed at 1640V, 200Ω, and 25 µF for a total pulse time of approximately 4 ms. Immediately after pulsing 1 mL of YPDS media was added to the cuvette and the entire mixture was thoroughly mixed by pipetting. The cuvette was then placed in a 27° C. incubator, without shaking, for 2 hours, after which 300 µL was streaked onto fresh PAD plates. These plates were incubated at 27° C. for approximately 7-10 days to promote cell growth.

4. Screening & Protein Expression

A color based screen was used to identify positive yeast cell transformants. White colonies are indicative of positive expression of the gene of interest, whereas red colonies indicate no expression. Accordingly, white colonies were selected from the PAD plates and re-streaked onto fresh PAD plates that were incubated for 3-5 days to promote the growth of individual colonies. A single colony was then used to inoculate 10 mL of BMGY medium placed in a 125 mL baffled flask that was incubated overnight with shaking (270 rpm) at 27° C. The optical density (OD) at 600 nm ($OD_{600}$) was periodically measured for a 1:10 diluted sample of the culture.

Incubation was stopped when the inoculum culture attained an $OD_{600}$ of 1.2-1.5 units. The inoculum was then transferred to a 50 mL conical tube and centrifuged at 5200 rpm for 5 minutes to pellet the cells. After decanting the supernatant 1 mL of fresh BMMY medium was added to pellet, following which the tube was covered with an air porous tape that permits sterile air exchange and placed in a shaking incubator at 27° C.

After 24 hours a 100 μl of the cell sample was removed to which was added 100 μl of 40% methanol to induce enzyme production. This methanolic sample was then centrifuged at 12,000 rpm for 5 minutes and the supernatant and pellet were saved as the T1 sample. A second culture sample was obtained after a 48 hour incubation period and treated with methanol as described above. After centrifugation, the supernatant and pellet are saved as the T2 sample. At 72 hours the entire incubation mixture is treated with an appropriate volume of 40% methanol. The supernatant and pellet obtained from methanolic treatment of the culture after a 72 hour incubation period is labeled as T3. The T3 supernatant was spun through an Amicon 30 kD protein filter and analyzed for protein using an SDS-PAGE gel.

Commercial amounts of THCA synthase or CBDA synthase were obtained by scaling up the volume of the culture using a fermentor. Thus, an yeast inoculum was first prepared by contacting 10 mL of BMGY medium in a 125 mL baffled flask with a single white colony of yeast. This starter culture was incubated overnight at 27° C. with shaking at 270 rpm to obtain culture with an $OD_{600}$ between 1.2 and 1.5 units. This starter culture was used to inoculate 90 mL of BMGY medium in a 1 L baffled flask. When the OD600 of this culture reached 1.2-1.5 units, the inoculum was transferred to a 500 mL centrifuge bottle and the yeast cells pelleted at 5200 rpm for 5 minutes.

5. Enzymatic Conversion.

The catalytic activity of THCA synthase was measured by incubating 25 μl of the cell free supernatant from a T3 sample with 25 μl of a 1 mg/ml CBGA stock in 200 μl of a 100 mM citrate buffer at pH 4.8 having 10% DMSO for 2 hours at 30° C. The final concentration of CBGA in the reaction mixture was 0.1 mg/ml and the final pH is 5.0. Table 4 illustrates the data related to the catalytic activity of THCA synthase obtained from independent colonies of transformed pPink yeast cells, namely. pPink yeast cells that were transformed using linearized THCA synthase plasmids. Culture samples that converted greater than 20% of the substrate CBGA to product THCA were selected for scale up.

TABLE 4

| Sample ID | % Conversion of CBGA to THCA in reaction containing 0.1 mg/ml CBGA. |
|---|---|
| Spe THC #3 | 20.6 |
| Spe THC #4 | 28.7 |
| Spe THC #22 | 20.6 |
| Spe THC #23 | 18.7 |
| Pme THC #5 | 32.5 |
| Pme THC(2) #1 | 29.1 |
| Pme THC(2) #2A | 27.2 |
| Pme THC(2) #25 | 31.6 |
| Pme THC(2) #36 | 27.7 |
| Pme THC(2) #41 | 32.5 |
| Pme THC(2) #42 | 27.6 |
| Pme THC(2) #46 | 40.7 |
| Pme THC(2) #51 | 26.8 |
| Pme THC(3) #1 | 55.2 |
| Pme THC(3) #11 | 35.0 |
| Pme THC(3) #17 | 69.9 |
| Pme THC(3) #19 | 36.8 |
| Pme THC(3) #20 | 34.3 |

6. Cloning Strategy for Generating Multi-Copy GOI Inserts In Vitro.

As described above, transformed cells having 6-10 copies of the gene of interest can be used to potentially boost up the production of heterologous protein. An alternate yeast expression system was used to obtain transformed cells having multiple copies of the gene of interest. The multi-copy *Pichia* Expression Kit from Invitrogen was used to construct a new plasmid that permits yeast cells to be transformed with multiple copies of the plasmid.

Briefly, the pAO815 vector was used to clone the gene of interest, Thus, the genes for α-CBDA synthase and α-THCA synthase were cut from pPink-HC plasmid using EcoR I and Bam HI restriction enzymes. 100 ng of the pPink-HC vector containing the α-CBDA synthase gene or the α-THCA synthase gene was incubated with 1 μl of EcoR I buffer, 1 ul of each restriction enzyme (10 units/ul) and 1 ul of BSA in a total reaction volume of 20 ul at 37° C. for 2 hr. Separately, 100 ng of pAO815 vector was digested with Eco R I and Bam HI enzymes using the protocol described above.

The digestion mixture is then loaded onto a 0.8% Agarose gel and the DNA fragments were separated from each other by electrophoresis at 95V for 1 hr. Bands corresponding the THCA synthase or CBDA synthase genes were extracted from the gel using the Invitrogen gel extraction kit. These gene fragments were ligated to a linearized pAO815 vector using T4 DNA ligase and following the ligation protocol from NEB®.

Following ligation, the circular vector containing the gene of interest was transformed into *E. coli* Top 10 F⁻ cells by electroporation at 1500 V, 200Ω and 25 μF for 4 ms. The transformed cells were then mixed with 250 ul of SOC medium (provided with One Shot® Top 10 Electrocomp™ *E. coli* from Invitrogen) and plated on a LB-Amp100 plate at 37 degrees overnight.

After incubation positive colonies were identified using the colony PCR protocol that relies on 5' AOX1 and 3'AOX1 primers for performing PCR. Positive colonies containing the gene of interest were grown in liquid LB-Amp100 media overnight at 37° C. The next day plasmid mini-preps were done using Invitrogen's fast prep kit and the concentration of the plasmid was analyzed on 0.8% Agarose gel before further amplification.

Once alpha-THCA synthase and alpha-CBDA synthase genes are inserted into pAO815, the recombinant plasmid is divided into 2 batches. The first batch was used as a vector in which was inserted a second copy of the gene of interest. The second batch of pAO815 recombinant plasmids was used for extracting the alpha-THCA synthase or alpha-CBDA synthase genes. Accordingly, the pAO815 recombinant plasmids used as vectors were first digested with Bam HI restriction enzyme following NEB's single digest protocol. Concurrently, the second batch of pAO815 recombinant plasmids were digested with Bgl II and Bam HI restriction enzymes.

The first and second digestion mixtures were purified using a 0.8% agarose gel followed by extraction of the purified linearized vector and alpha-THCA synthase or alpha-CBDA synthase gene sequences from the gel. Each gene sequence was then ligated with the linearized vector following NEB's T4 DNA ligase protocol and the vectors containing the gene were used to transform *E. coli* Top10 F⁻ cells by electroporation. The transformed cells were incubated at 37° C. overnight and then screened for the correct gene insert. The above protocol is repeated several times to obtain a multi-copy insert plasmid. After confirming the sequence identity of the gene insert, the multi-copy plasmid was linearized at the His4 sequence region by restriction enzyme digestion and used to transform competent *Pichia pastoris* strain G115 (his4, Mut+) cells. The transformed cells were grown on His⁻ plates for screening. Screening was done on His⁻ plates to confirm integration of the plasmid at the His site of the *Pichia Pastoris* genome. Positive colonies were chosen for methanol induction of protein, and the activity of the secreted protein was assayed using protocols described above.

Chemical Synthesis

A. Synthesis of Geraniol
(3,7-Dimethylocta-2,6-dien-1-ol,)

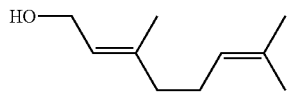

Geraniol was obtained by distillation of palmarosa oil. Palmarosa oil (New Directions Aromatics) was distilled under reduced pressure and the fractions that distil between 139-145° C. and under a reduced pressure of 25 mm Hg were pooled to obtain pure geraniol.

B. Synthesis of Olivetol

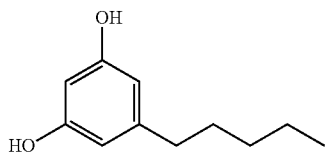

Olivetol was synthesized using a published procedure (Focella, A, et al., *J. Org. Chem.*, Vol. 42, No. 21, (1977), p. 3456-3457).

1. Methyl 6-N-Pentyl-2-hydroxy-4-oxo-cyclohex-2-ene-1-carboxylate

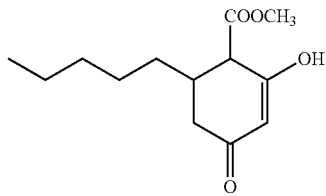 [SMILES: CCCCCC1CC(=O)C=C(O)C1C(=O)OC]

To a stirring solution of sodium methoxide (32.4 g, 0.60 mol) and dimethyl malonate (90 g, 0.68 mol) in 230 mL of anhydrous methanol was added portion wise 75 g (0.48 mol) of 90% 3-nonen-2-one. The reaction mixture was then refluxed for 3 h under $N_2$ and allowed to cool to room temperature. The solvent was distilled under reduced pressure and the residue dissolved in 350 mL of water. The slurry of white crystals and the almost clear solution was extracted thrice with 80 mL of chloroform. The aqueous layer was acidified to pH 4 with concentrated HCl and the white precipitate that formed was allowed to stand overnight prior to filtration. The crystals were dried at 50° C. under high vacuum for 5 hours to yield 106.5 g (0.4416 mol) (92%) of methyl 6-n-Pentyl-2-hydroxy-4-oxo-cyclohex-2-ene-1-carboxylate (mp 96-98 C). The product was recrystallized using a mixture of petroleum ether:ethyl acetate (9:1), and gave 94 g of pure methyl 6-n-Pentyl-2-hydroxy-4-oxo-cyclohex-2-ene-1-carboxylate (melting point of 98-100 C).

2. 1-N-Pentyl-3,5-dihydroxybenzene (Olivetol)

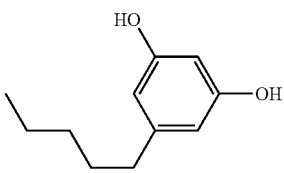

To a stirring ice-cooled solution of methyl 6-N-pentyl-2-hydroxy-4-oxo-cyclohex-2-ene-1-carboxylate (58.4 g, 0.24 mol) dissolved in 115 mL dimethylformamide was added dropwise 37.9 g (0.23 mol) of bromine dissolved in 60 mL of dimethylformamide. At the end of the addition (ca. 90 min) the reaction mixture was slowly heated to 80° C. during which time the evolution of carbon dioxide became quite vigorous.

The reaction was maintained at this temperature until gas evolution had ceased following which the reaction was further heated to 160° C. and held at this temperature for approximately 10 hours. After heating, the reaction was allowed to cool and the solvent DMF was removed under reduced pressure. The residue thus obtained was treated with water (80 mL) and extracted twice with 250 mL of ether. The combined ether layers were washed with water, then washed with 2×80 mL of a 10% solution of sodium bisulfite, 2×80 mL of a 10% solution of acetic acid, and then again with water.

After drying over anhydrous sodium sulfate the solvent was removed under reduced pressure to give 46.8 g of a viscous oil. The oil was distilled under reduced pressure to give 30.3 g (0.168 mol) (69.3%) of olivetol as product. HPLC analysis indicated 97.5% purity.

C. Synthesis of CBG

CBG was synthesized following the protocol disclosed by Taura et al., (1996), *The Journal of Biological Chemistry*, Vol. 271, No. 21, p. 17411-17416.

1. Synthesis of 2-[(2E)-3,7-dimethylocta-2,6-dienyl]-5-pentyl-benzene-1,3-diol (Cannabigerol (CBG))

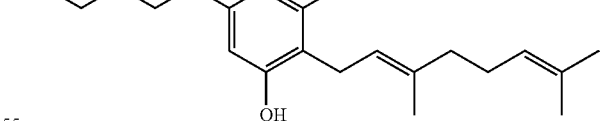

Geraniol (3 g, 0.0194 mol) and olivetol (2 g, 0.0111 mol) were dissolved in 400 mL of chloroform containing 80 mg of p-toluenesulfonic acid as catalyst and the reaction mixture was stirred at room temperature for 12 h in the dark. After 12 hours, the reaction mixture was washed with saturated sodium bicarbonate (400 mL) and then with $H_2O$ (400 mL). The chloroform layer was concentrated at 40 C under reduced pressure, and the residue obtained was chromatographed on a 2.0 cm×25 cm silica gel column using benzene (1000 mL) as the eluent to give 1.4 g (0.00442 mol)(39.9%) CBG as product.

Alternatively crude CBG was purified as follows. To a 250 mL beaker was added 7.25 g crude CBG and 50 mL benzene. The flask was swirled to dissolve the CBG and 50 g silica gel was added, along with a stir bar. The solution was stirred overnight, and then poured into a 44 cm×2.75 cm column. The column was eluted with 300 mL benzene. The eluent, approximately 70 ml, fractions were assayed for CBG. Fractions 1, 2, and 3 (~230 mL) that contained CBG were combined and the solvent removed under pressure to give 6.464 g residue containing >80% CBG, having a purity suitable for use in the next synthetic step.

In one embodiment, crude CBG was purified by mixing 7.25 g crude CBG residue with a slurry of silica gel (50 mL), in a 250 ml Beaker. This mixture was slowly agitated for 1 hour and then vacuum filtered using a fine mesh filter paper. The filter cake was washed with 250 ml benzene until a clear filtrate was obtained. The solvent from the filtrate was removed under reduced pressure to give 6.567 g of a residue having >80% CBG.

2. Synthesis of CBG-Acid (CBGA)

?A. Synthesis of Methylmagnesium Carbonate (MMC)

Methylmagnesium Carbonate (MMC) was synthesized following the protocol disclosed by Balasubrahmanyam et al., (1973), *Organic Synthesis, Collective Volume V*, John Wiley & Sons, Inc., p. 439-444.

A dry 2 liter, three necked flask was fitted with a mechanical stirrer, a condenser, and a 1 liter, pressure-equalizing addition funnel, the top of which was fitted with a gas inlet tube. A clean, dry magnesium ribbon (40.0 g, 1.65 mol) was placed in the flask and the system was flushed with nitrogen prior to the addition of anhydrous methanol (600 mL). The evolution of hydrogen gas was controlled by cooling the reaction mixture externally. When hydrogen evolution had ceased, a slow stream of nitrogen was passed through the system and the condenser was replaced by a total condensation-partial take-off distillation head. The nitrogen flow was stopped and the bulk of the methanol distilled from the solution under reduced pressure. Distillation was stopped when stirring of the pasty suspension of magnesium methoxide was no longer practical. The system was again flushed using nitrogen and the outlet from the distillation head was attached to a small trap containing mineral oil so that the volume of gas escaping from the reaction system could be estimated.

Anhydrous dimethylformamide (DMF)(700 mL) was added to the reaction flask, and the resulting suspension was stirred vigorously while a stream of anhydrous carbon dioxide was passed into the reaction vessel through the gas inlet tube attached to the addition funnel. The dissolution of carbon dioxide was accompanied by an exothermic reaction with the suspended magnesium methoxide. When no more $CO_2$ is absorbed, the colorless solution was heated under a slow stream of $CO_2$ gas until the temperature of the liquid distilling reached 140° C., indicating that residual methanol had been removed from the reaction mixture. The reaction mixture was flushed using a slow stream of nitrogen to aid in cooling the mixture to room temperature under an inert atmosphere. This yielded a solution having 536 mg MMC/mL of DMF.[8]

B. Formation of CBG-A 6-carboxylic acid-2-[(2E)-3,7-dimethylocta-2,6-dienyl]-5-pentyl-benzene-1,3-diol, Cannabigerolic Acid (CBGA) was prepared as follows. To a 10 mL conical flask was added 1 mL of a DMF solution of MMC. To this solution was added 2-[(2E)-3,7-dimethylocta-2,6-dienyl]-5-pentyl-benzene-1,3-diol (120 mg, 0.379 mmol). The flask was heated at 120° C. for 1 hour, following which the reaction mixture was dissolved in 100 mL of chloroform:methanol (2:1) solution. The pH of this solution was adjusted with dilute HCl to pH 2.0, and then partitioned using 50 mL $H_2O$.

The organic layer was dried over sodium sulfate and the solvent was removed by evaporation. HPLC analysis of the crude reaction showed ~40% conversion of CBG to CBG-A Alternatively, 3.16 g (10 mmols) of CBG (or any other neutral cannabinoid), 8.63 g (100 mmols) magnesium methylate and 44 g (1 mol) of dry ice were sealed in a pressure compatible vessel. The vessel is heated to 50° C., and the temperature held at this value for three hours. Following heating, the vessel is cooled to room temperature and slowly vented. The reaction mixture was dissolved in 100 mL of a chloroform: methanol (2:1) solvent. The pH of this solution was adjusted with dilute HCl to pH 2.0 and this solution was then partitioned using 50 mL of $H_2O$. The organic layer was dried over sodium sulfate and the solvent was removed by evaporation. HPLC analysis of crude reaction mixture shows ~85% conversion of CBG to CBG-A using this protocol.

Crude CBG-A was purified by chromatography using a 2.0 cm×25 cm silica gel column. The product was eluted using a mixture of n-hexane:ethyl acetate (2:1) (1000 mL), to obtain 45 mg (0.125 mmol)(37.5%) of the desired product.

Alternatively, ultra high purity CBGA was obtained by chromatographing the crude using LH-20 lipophilic resin as the medium. 400 g of LH-20 Sephadex resin was first swollen using 2 L of DCM:chloroform (4:1) solvent. The swollen resin was gravity packed in a 44×2.75 cm column. The column was loaded with 2.1 g of crude CBGA dissolved in a minimum amount of DCM:chloroform (4:1) solvent and eluted with 1.7 L of the same solvent. 100 mL fractions were collected. The unreacted CBG was eluted as a yellow/orange solution using this solvent system. After the passage of about 1.7 L of this solvent, no more yellow/orange fraction were observed and the eluting solvent was changed to 100% acetone to elute the bound CBGA.

The fractions containing CBGA were pooled and the solvent was removed to obtain 0.52 g CBGA (~90% recovery). Increasing the volume of DCM:chloroform (4:1) solvent passed through the column prior to eluting with acetone, yielded CBGA having purity greater than 99.5%.

Synthesis of CBGV

CBGV was synthesized as follows.

A. Methyl 6-N-Propyl-2-hydroxy-4-oxo-cyclohex-2-ene-1-carboxylate

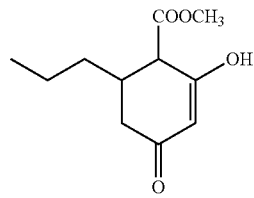

Briefly, 3-hepten-2-one (30.1 g, 0.25 mol) was added dropwise to a dry methanolic (125 mL dry MeOH), solution of diethyl malonate (52.016 g, 0.323 mol) and sodium methoxide (16.206 g, 0.3 mol). The crude product weighed 46.315 g upon drying at 45° C. overnight in a vacuum oven. The crude product was dissolved in petroleum ether (300 mL). After stirring, any undissolved material was filtered from the solution prior to the addition of ethyl acetate (30 mL), to precipitate CBGV. The precipitate was filtered and dried overnight at 44° C. in a vacuum oven. A total of 33.569 g (0.157 mol) (52.3%) of the desired product was recovered.

B. 1-N-Propyl-3,5-dihydroxybenzene

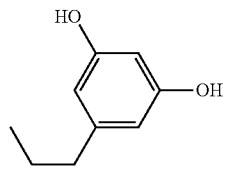

A procedure similar to the one described above for the synthesis of olivetol was used to manufacture the titled compound, except that methyl 6-N-propyl-2-hydroxy-4-oxo-cyclohex-2-ene-1-carboxylate was used as the starting material. Briefly, to a stirring ice cold DMF solution of methyl 6-N-propyl-2-hydroxy-4-oxo-cyclohex-2-ene-1-carboxylate was added a DMF solution of bromine. Following the addition of bromine the reaction mixture was heated to 80° C. Heating was accompanied by the generation and release of carbon dioxide gas. After gas evolution has ceased, the temperature of the reaction was increased to 160° C. and heating was continued for 10 hours. The reaction was then cooled and DMF was removed under reduced pressure. The crude mixture was diluted with water and subjected to solvent extraction using diethyl ether. The titled compound was obtained by removing the ether and distilling the oil that remains.

C. 2-[(2E)-3,7-dimethylocta-2,6-dienyl]-5-propyl-benzene-1,3-diol, (CBGV)

The synthesis of CBGV proceeded by adding p-toluenesulfonic acid to a chloroform solution of geraniol and 1-N-Propyl-3,5-dihydroxybenzene. After stirring the reaction at room temperature in the dark for 12 hours, water was added to partition the crude product into the chloroform layer. The chloroform layer was then washed with saturated sodium bicarbonate, dried and the organic solvent removed prior to purification as described above for the synthesis of CBG.

D. 6-carboxylic acid-2-[(2E)-3,7-dimethylocta-2,6-dienyl]-5-propyl-benzene-1,3-diol (CBGVA)

6-carboxylic acid-2-[(2E)-3,7-dimethylocta-2,6-dienyl]-5-propyl-benzene-1,3-diol, cannabigerolic Acid (CBGVA) was prepared as follows. Methyl magnesium carbonate (MMC) was prepared as described above. To a DMF solution of MMC in a flask was added 2-[(2E)-3,7-dimethylocta-2,6-dienyl]-5-propyyl-benzene-1,3-diol. The flask was heated at 120° C. for 1 hour, following which the reaction mixture was dissolved in a 2:1 mixture of chloroform:methanol. The pH of this solution was adjusted with dilute HCl to pH 2.0, and the reaction mixture was extracted using $H_2O$.

The organic layer was dried over sodium sulfate and the solvent was removed by evaporation to afford the titled compound CBGVA as the crude product.

Large Scale Enzymatic Production of Cannabinoids 100 ml of a 10 mM sodium phosphate buffer (pH 5.0) were placed in a glass reaction vessel equipped with oxygen gas sparger and a stirrer. To this solution 35 g/l of either 2-hydroxypropyl-β-cyclodextrin (HPβCD; Kleptose® HPB), a sulfobutylether β-cyclodextrin sodium salt (SBEβCD; Captisol®), or a randomly methylated β-cyclodextrin (RMβCD) were added. The CD was added in small 5 g portions to ensure full dissolution.

2.5 g of a cannabinoid synthase substrate, for example, CBGA or CBGV-A or a Formula I, II or V compound, were added to the buffered cyclodextrin solution. The molar ratio of CD to substrate was about 4:1. 60 mg of purified synthase were added to the solution and the reaction mixture was incubated at 30° C. for 8 hours. Progress of the reaction was periodically monitored by HPLC, and using an enzymatic assay to detect and quantify the evolution of hydrogen peroxide.

After 8 hours, greater than 90% of a CBGA substrate was converted to THCA and CBCA. The ratio of THCA to CBCA was approximately 10:1 at an acidic pH of 5.0. The ratio of the CBC isomers was 5:1.

The aqueous solution was diluted 10:1 with 95% EtOH. This causes cyclodextrin to precipitate out leaving the cannabinoids in solution. The cyclodextrin was vacuum filtered, washed with 1 L of 90% EtOH, and dried to permit its reuse in a future reaction. Concentration of the ethanolic solution containing the cannabinoids followed suspension of the residue in DCM:chlorofrom (4:1) solvent yields ~25 g crude orange-yellow residue.

Large Scale Purification of Cannabinoids

Purification of cannabinoids synthesized using a method of this technology was accomplished chromatographically using LH-20 lipophilic resin. Briefly, 4000 g of the resin was swollen using 20 L of DCM:chloroform (4:1). The swollen resin was gravity packed in a 44×27.5 cm column. The volume of the swollen resin is ~1350 mL. The column was loaded with 25 g crude residue dissolved in a minimum amount of the solvent and then washed with 4 L DCM:chloroform (4:1) solvent to elute CBG. No cannabinoid acids were eluted from the column during this elution.

Gradient elution with a 1:1 to 0:1 DCM:acetone solvent was used to elute the cannabinoid acids. Each step of the gradient used one column volume (4 L) of solvent. CBCA eluted first, followed by CBGA, and then THCA. The purity of each cannabinoid was >99.5%.

The pure cannabinoids can further be processed to their neutral or "active" form by heating the acid forms at 90° C. under vacuum. Decarboxylation was quantitative to give the neutral cannabinoid. If necessary, recrystallization can be performed to obtain pharmaceutical grade cannabinoids.

What is claimed is:
1. An in vitro method for producing
   (a) tetrahydrocannabinolic acid (THCA) and cannabichromenic acid (CBCA) in different ratios, or
   (b) cannabidiolic acid (CBDA) and cannabichromenic acid (CBCA) in different ratios comprising the steps of:
   reacting cannabigerolic acid (CBGA) with a cannabinoid synthase in a reaction mixture; selecting the pH of the reaction mixture in a range between about 4.0 and about 8.0 to produce
   (i) tetrahydrocannabinolic acid (THCA) and cannabichromenic acid (CBCA) when the cannabinoid synthase is tetrahydrocannabinolic acid synthase (THCA synthase), or

(ii) cannabidiolic acid (CBDA) and cannabichromenic acid (CBCA) when the cannabinoid synthase is cannabidiolic acid synthase (CBDA synthase), and recovering the THCA and CBCA or CBDA and CBCA so produced.

2. The method of claim 1, wherein the cannabinoid synthase is tetrahydrocannabinolic acid synthase (THCA synthase).

3. The method of claim 2, wherein the cannabinoid synthase is immobilized on a solid support.

4. The method of claim 1, wherein the cannabinoid synthase is a recombinant cannabinoid synthase, and the method further comprises producing the recombinant cannabinoid synthase.

5. The method of claim 4, wherein the step of producing recombinant THCA synthase comprises overexpressing the THCA synthase.

6. The method of claim 5, wherein the THCA synthase is expressed in yeast or in *Escherichia coli*.

7. The method of claim 1, wherein the reaction mixture comprises a solvent, which is one or more of dimethyl sulfoxide (DMSO), dimethyl formamide (DMF), iso-propoyl alcohol and cyclodextrin, and wherein the amount of the solvent in the reaction mixture is between 5% and 30% (w/v).

8. An ex vivo method for producing the products tetrahydrocannabinolic acid (THCA) and cannabichromenic acid (CBCA) in different ratios comprising the steps of:

reacting cannabigerolic acid (CBGA) with tetrahydrocannabinolic acid synthase (THCA synthase) in a reaction mixture;

modifying the pH of the reaction mixture in a range from about 4.0 and about 8.0 to produce tetrahydrocannabinolic acid (THCA) and cannabichromenic acid (CBCA) in different ratios; and recovering the THCA and CBCA so produced.

9. The method of claim 8, wherein the THCA synthase is immobilized on a solid support.

10. The method of claim 8, wherein the THCA synthase is a recombinant THCA synthase, and the method further comprises producing recombinant THCA synthase.

11. The method of claim 10, wherein the step of producing recombinant THCA synthase in large scale comprises overexpressing the THCA synthase.

12. The method of claim 11, wherein the THCA synthase is expressed in yeast or in *Escherichia coli*.

13. The method of claim 8, wherein the reaction mixture comprises a solvent, which is one or more of dimethyl sulfoxide (DMSO), dimethyl formamide (DMF), iso-propoyl alcohol and cyclodextrin, and wherein the amount of the solvent in the reaction mixture is between 5% and 30% (w/v).

14. An ex vivo method for producing the products cannabidiolic acid (CBDA) and cannabichromenic acid (CBCA) in different ratios comprising the steps of:

reacting cannabigerolic acid (CBGA) with cannabidiolic acid synthase (CBDA synthase) in a reaction mixture;

modifying the pH of the reaction mixture in a range between about 4.0 and about 8.0 to produce cannabidiolic acid (CBDA) and cannabichromenic acid (CBCA) in different ratios; and recovering the CBDA and CBCA so produced.

15. The method of claim 14, wherein the CBDA synthase is immobilized on a solid support.

16. The method of claim 14, wherein the CBDA synthase is a recombinant CBDA synthase, and the method further comprises producing recombinant CBDA synthase.

17. The method of claim 16, wherein the step of producing recombinant CBDA synthase comprises overexpressing the CBDA synthase.

18. The method of claim 17, wherein the CBDA synthase is expressed in yeast or in *Escherichia coli*.

19. The method of claim 14, wherein the reaction mixture comprises a solvent, which is one or more of dimethyl sulfoxide (DMSO), dimethyl formamide (DMF), iso-propoyl alcohol and cyclodextrin, and wherein the amount of the solvent in the reaction mixture is between 5% and 30% (w/v).

\* \* \* \* \*